United States Patent
Ide

(10) Patent No.: US 8,352,017 B2
(45) Date of Patent: Jan. 8, 2013

(54) BONE DENSITY METER

(75) Inventor: Kazuhiro Ide, Takatsuki (JP)

(73) Assignee: Panasonic Electric Works Co., Ltd. (JP)

( * ) Notice: Subject to any disclaimer, the term of this patent is extended or adjusted under 35 U.S.C. 154(b) by 577 days.

(21) Appl. No.: 12/582,231

(22) Filed: Oct. 20, 2009

(65) Prior Publication Data

US 2010/0105995 A1 Apr. 29, 2010

(30) Foreign Application Priority Data

Oct. 27, 2008 (JP) ................................ 2008-275945

(51) Int. Cl.
*A61B 6/00* (2006.01)
(52) U.S. Cl. ...................................................... 600/476
(58) Field of Classification Search .................. 600/310, 600/476
See application file for complete search history.

(56) References Cited

U.S. PATENT DOCUMENTS

| | | | |
|---|---|---|---|
| 5,840,029 A | 11/1998 | Mazess et al. | |
| 6,456,870 B1 * | 9/2002 | Rennert et al. | 600/475 |
| 6,570,955 B1 * | 5/2003 | Siffert et al. | 378/54 |
| 7,112,173 B1 * | 9/2006 | Kantorovich et al. | 600/449 |
| 2001/0004394 A1 * | 6/2001 | Siffert et al. | 378/56 |
| 2002/0002336 A1 | 1/2002 | Marchitto et al. | |
| 2002/0156378 A1 | 10/2002 | Sakai | |
| 2003/0009089 A1 | 1/2003 | Rennert et al. | |
| 2003/0139667 A1 | 7/2003 | Hewko et al. | |
| 2004/0068166 A1 * | 4/2004 | Faulkner et al. | 600/407 |

FOREIGN PATENT DOCUMENTS

| | | |
|---|---|---|
| DE | 102005029189 A1 | 12/2006 |
| FR | 2852101 A1 | 9/2004 |
| JP | 2005-245724 | 9/2005 |
| JP | 2007-007267 | 1/2007 |
| JP | 2007-190272 | 8/2007 |
| JP | 2008-102728 | 5/2008 |
| JP | 2008-155011 | 7/2008 |
| KR | 20040085124 A | 7/2004 |
| WO | 0163251 A1 | 8/2001 |
| WO | 2005004714 A1 | 1/2005 |

OTHER PUBLICATIONS

Machine translation of Tanaka et al. (JP 2008-155011A).*
Office Action issued Aug. 17, 2010 for JP Patent Application No. 2008-275945.
Office Action for Chinese Application No. 200910205067.8 issued Feb. 28, 2011. European Search Report for Application No. 09173542.3-2319/2179689 issued May 7, 2010.
Office Action issued on Apr. 11, 2011 for EP Application No. 09 173 542.3.
International Search Report for Application No. EP 09 17 3542 dated Jan. 29, 2010.

* cited by examiner

*Primary Examiner* — Eric Winakur
*Assistant Examiner* — Linda B Smith
(74) *Attorney, Agent, or Firm* — Caesar, Rivise, Bernstein, Cohen & Pokotilow, Ltd.

(57) ABSTRACT

A bone density meter including a light emission unit which emits light toward a surface of a user's body. A light reception unit receives the light emitted from the light emission unit toward the body surface and propagated in a portion of the body that includes bone. A bone density computation unit determines the bone density based on the amount of light received by the light reception unit. The light emission unit emits light toward the body surface at a portion having a thin subcutis, and the light reception unit receives the light propagated in the body through the portion at which the subcutis is thin.

7 Claims, 7 Drawing Sheets

BONE DENSITY METER

CROSS-REFERENCE TO RELATED APPLICATIONS

This application is based upon and claims the benefit of priority from prior Japanese Patent Application No. 2008-275945, filed on Oct. 27, 2008, the entire contents of which are incorporated herein by reference.

BACKGROUND OF THE INVENTION

The present invention relates to a bone density meter that uses light to measure bone density.

Methods for measuring the bone density of a measurement subject, such as a person, using light are known in the prior art. Japanese Laid-Open Patent Publication No. 2008-155011 describes one example of a bone density meter. The bone density meter includes a light emission unit, a light reception unit, a variation tendency calculation means, and a density calculation means. The light emission unit emits light into the measurement subject as it varies the light intensity. The light reception unit receives the reflection of the emitted light from the measurement subject. The variation tendency calculation means calculates a variation tendency from the intensity of the reflection light. The density calculation means calculates the bone density of the measurement subject from the variation tendency. In this manner, the bone density meter of the prior art varies the intensity of the light emitted from the light emission unit to evaluate and measure the bone density from the variation in the intensity of the reflection light.

In the bone density meter of the prior art, when measuring the bone density, for example, at a portion at which the subcutis is thick, light may not reach the bone due to factors such as insufficient output of the light emission unit. In such a case, accurate detection of the bone density is difficult.

SUMMARY OF THE INVENTION

The present invention relates to a bone density meter that provides more accurate measurement of bone density using light.

One aspect of the present invention is a bone density meter for measuring bone density of a user. The bone density meter includes a light emission unit which emits light toward a surface of the body of the user. A light reception unit receives the light emitted from the light emission unit toward the body surface and propagated through a portion of the body that includes bone. A bone density calculation unit determines the bone density based on the amount of light received by the light reception unit. The light emission unit emits light toward the body surface at a portion having a thin subcutis. The light reception unit receives the light propagated in the body through the portion at which the subcutis is thin.

Other aspects and advantages of the present invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which.

DETAILED DESCRIPTION OF THE PREFERRED EMBODIMENTS

Figure 1:
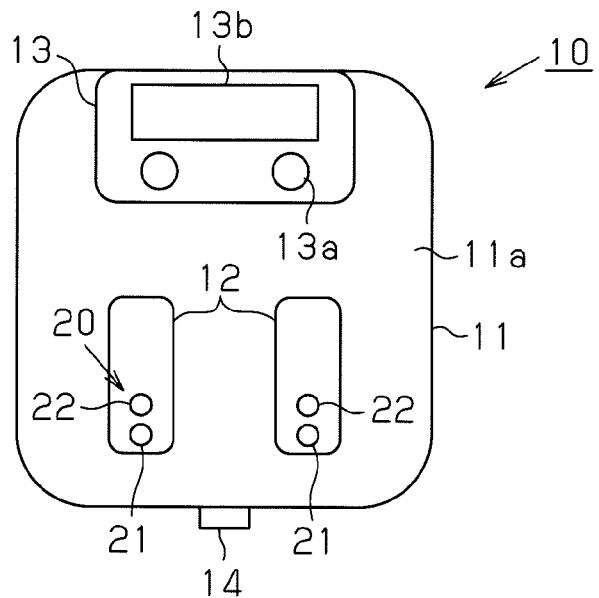
FIG. 1 is a schematic diagram showing a preferred embodiment of a bone density meter according to the present invention.

In the drawings, like numerals are used for like elements throughout.

A preferred embodiment of a bone density meter according to the present invention will now be discussed with reference to the drawings.

FIG. 1 schematically shows the structure of a bathroom scale 10 to which the bone density meter is applied. The bathroom scale 10 includes a platform 11, which is box-shaped so that a user can stand on it. The platform 11 has an upper surface 11a. A footrest 12 is formed on the upper surface 11a of the platform 11. An operation unit 13 is removably attached to the front part of the platform 11. A power switch 14 is arranged in the rear side (lower side) of the platform 11. A load sensor (not shown) such as a load cell is arranged in the platform 11. Accordingly, the bathroom scale 10 also functions as a weighing scale in this embodiment.

Figure 2:
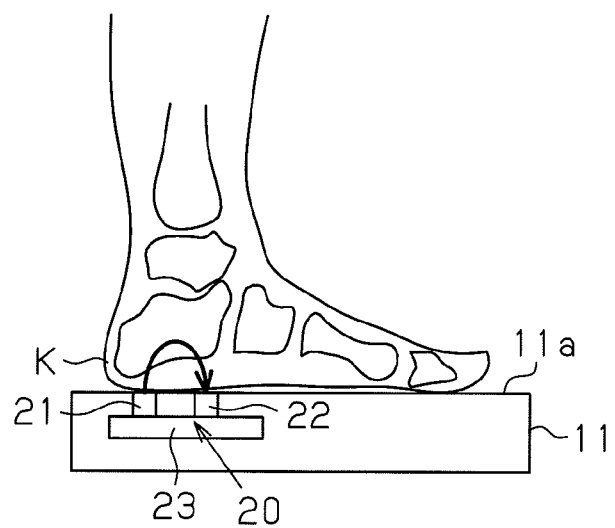
FIG. 2 is a schematic side view showing the bone density meter of FIG. 1.

A bone density meter 20 is arranged at the rear portion of the footrest 12 to measure the bone density of, particularly, the user's heel K. Referring to FIG. 2, the bone density meter 20 includes a light emission unit 21, which emits light towards the user's heel K, and a light reception unit 22, which receives the light emitted from the light emission unit 21 and propagated through a portion of the user's body that includes bones, as reflection light. The light emission unit 21 is formed, for example, by a light-emitting diode (LED) having a center wavelength of 800 nm. The light reception unit 22 is formed by a photodiode. The wavelength of the light emitted from the light emission unit 21 may be changed as long as it is in the range of 500 nm to 2500 nm. Light having a wavelength in this range is highly transmissive through a user's body, such as through a bone or subcutis. Light having a wavelength close to 500 nm is visible and thereby allows the user to be aware that the bathroom scale 10 is functioning.

Figure 3:
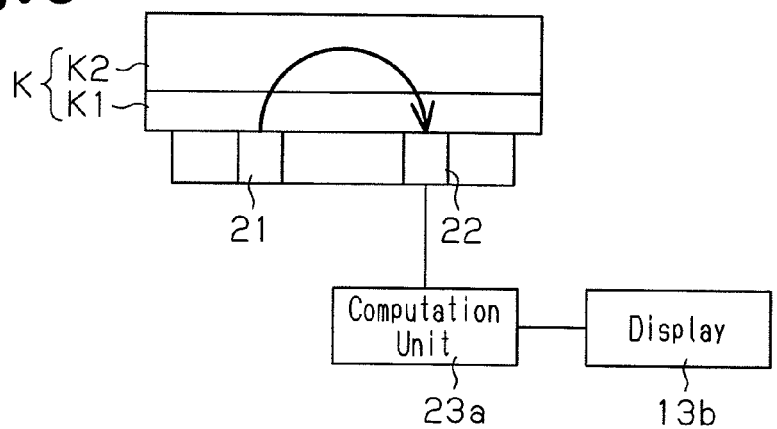
FIG. 3 is a schematic diagram showing electrical connections in the bone density meter of FIG. 1.

A microcomputer 23 is arranged below and electrically connected to the light emission unit 21 and the light reception unit 22. The microcomputer 23 controls the light emission unit 21 and light reception unit 22. For example, as shown in FIG. 3, the light reception unit 22 is connected to a computation unit 23a arranged in the microcomputer 23 and serving as a bone density calculation unit. The computation unit 23a calculates, or determines, the bone density from the output (light amount) of the light reception unit 22.

As shown in FIG. 1, the operation unit 13 includes a measurement start button 13a, which instructs initiation of bone density measurement, and a display 13b, which shows various types of information. The operation unit 13 is connected by a connection cable (not shown) to the platform 11. The connection cable is wound in an extendible manner around a reel (not shown) arranged in the platform 11. The display 13b shows the bone density measurement result obtained by the computation unit 23a of the microcomputer 23 so that the user can easily check the measurement result.

In a state in which the user's soles are resting on the footrest 12, the user presses the measurement start button 13a of the operation unit 13 to operate the bathroom scale 10. When the bathroom scale 10 is functioning, the microcomputer 23 drives the light emission unit 21 and the light reception unit 22 at about the same time. The light emission unit 21 emits light toward the heel K. The light is propagated in the user's body as it is scattered and reflected by the subcutis K1 of the heel K (FIG. 3), the heel bone K2 (FIG. 3), and other parts before being received by the light reception unit 22. Then, the computation unit 23a of the microcomputer 23 calculates the bone density of the heel bone K2 in accordance with the amount of light received by the light reception unit 22. The bone density measurement result is shown on the display 13b of the operation unit 13. When the user's feet rest on the platform 11, the user's weight is applied to the platform 11. This stabilizes the state of the subcutis and bone density. Further, the user's feet blocks external light and increases measurement accuracy.

Figure 4A:
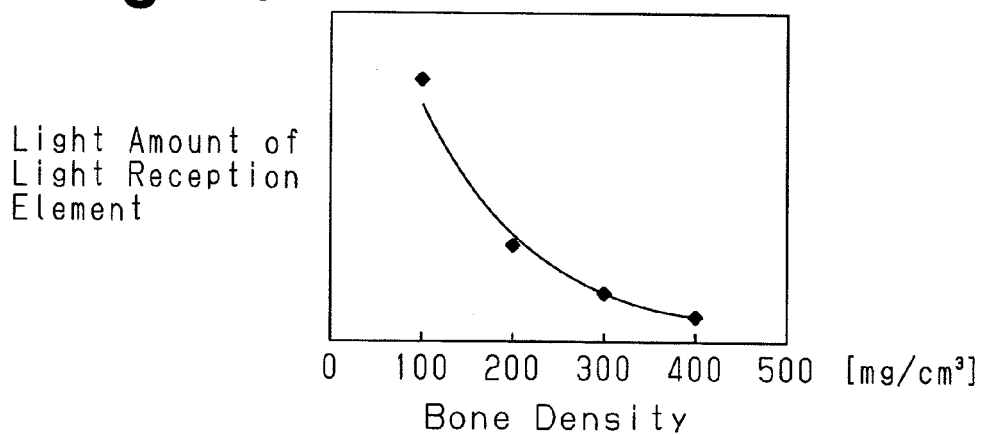
FIG. 4A is a schematic graph showing the relationship between the bone density and light reception amount.
Figure 4B:
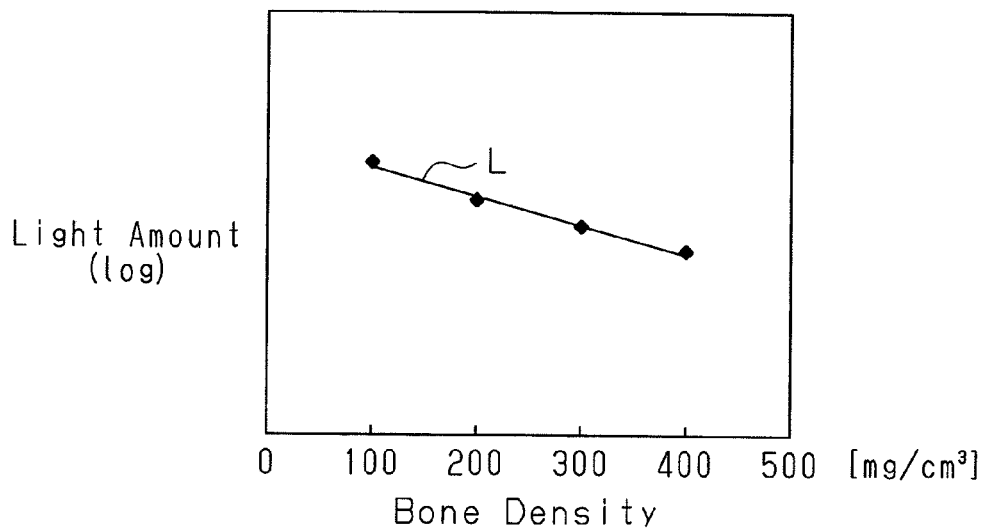
FIG. 4B is a schematic graph showing the light reception amount of FIG. 4A with a logarithm.
Figure 5:
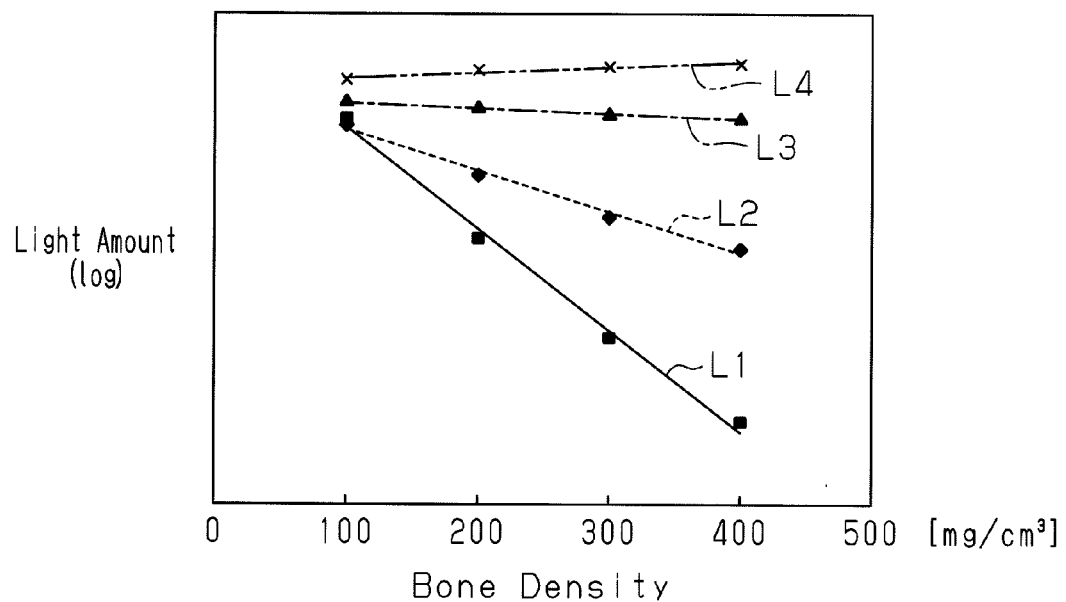
FIG. 5 is a schematic graph showing the relationship between the light reception amount and subcutis.

The relationship between the bone density and light reception amount and the relationship between the emitted light and subcutis will now be discussed with reference to FIGS. 4 and 5.

The inventor of the present invention conducted a modeling experiment to check the relationship between the bone density and light reception amount. Four bone phantoms of which the base compound was polyurethane was prepared. Hydroxylapatite, which is the main component of a bone, was applied to the four bone phantoms in amounts of 100, 200, 300, and 400 mg/cm$^3$, respectively. The bone phantoms were used to check the relationship of the bone density and the light amount received by the light reception unit 22. As apparent from the results, which are shown in FIG. 4A, the light amount decreases exponentially as the bone density increases. Further, when expressing the light amount with a logarithm, the relationship between the bone density and light amount is expressed by line L, which has a strong correlation (correlation coefficient r=0.99), as shown in FIG. 4B. Accordingly, it is apparent that the bone density is measurable from the light amount received by the light reception unit 22.

To consider the influence of the subcutis, particularly, subcutaneous fat, on the emitted light, the inventor of the present invention checked the influence of the subcutis on the bone density measurement using a simulated model. Here, four simulated models respectively having a subcutaneous fat thickness of 0 mm, 5 mm, 10 mm, and 20 mm were used. FIG. 5 shows the relationship between the bone density and light reception amount obtained as approximated lines L1 to L4 from the four simulated models. The reference characters L1 to L4 added to the approximate lines are in order from the thinnest subcutaneous fat. As shown in FIG. 5, as the subcutaneous fat thickness increases in the order of 0 mm, 5 mm, and 10 mm, variation in the received light amount relative to variation in the bone density becomes small. That is, the inclination of the approximate line becomes small. Further, when using the simulated model of which subcutaneous fat (subcutis) thickness is 20 mm and thereby greater than 10 mm, the light reception amount cannot follow the variation of the bone density. Accordingly, at a location at which the thickness of the subcutis is generally 10 mm or less (in the preferred embodiment, the heel), the light amount received by the light reception unit 22 is substantially unaffected by the subcutis. This allows for quantitative measurement of the bone density.

As described above, by measuring the bone density at the heel, at which the subcutis thickness is 10 mm or less, further accurate measurement results are obtained. Further, the user may easily measure the bone density just by standing on the platform 11.

The bone density meter 20 of the preferred embodiment has the advantages described below.

(1) The light emission unit 21 emits light toward the body surface at a portion in which the subcutis is thin (in the preferred embodiment, the heel K). The light reception unit 22 receives the light propagated in the body through the subcutis. This allows for the bone density to be measured at a portion in which the subcutis (subcutaneous fat) is thin. Thus, the light emitted from the light emission unit 21 easily reaches the bone. This suppresses the influence of the subcutis on the light and ensures measurement of the bone density. Further, the bone density is measured at the heel K from the sole. This also allows for easy scaling of the user's weight.

(2) The light emission unit 21 emits light having a wavelength of 800 nm, which is included in the range of 500 nm to 2500 nm. Thus, the bone density is measured using light having a wavelength that is highly transmissive in the user's body. Further, light is visible when emitted at a wavelength close to 500 nm. Thus, the emission of such light would allow the user to be aware that at least the bone density meter 20 is functioning in the bathroom scale 10.

It should be apparent to those skilled in the art that the present invention may be embodied in many other specific forms without departing from the spirit or scope of the invention. Particularly, it should be understood that the present invention may be embodied in the following forms.

In the preferred embodiment, the bone density meter 20 is used in combination with a weighing scale function in a bathroom scale 10. However, the bone density meter 20 does not have to be used in combination with other functions and may be provided as a single-purpose device.

Figure 6A:
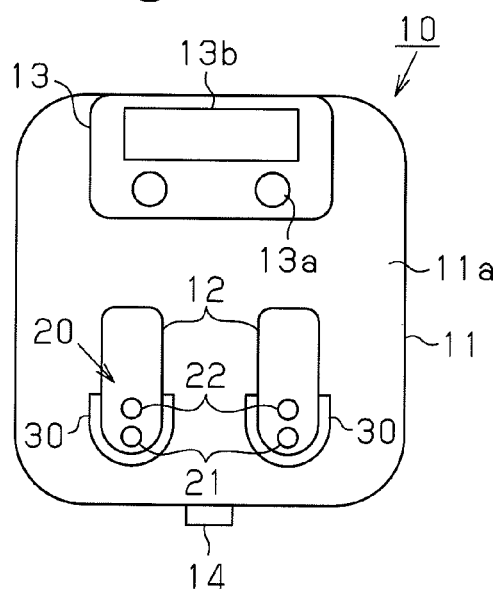
FIGS. 6A and 6B are schematic diagrams showing a bone density meter in a further example.
Figure 6B:
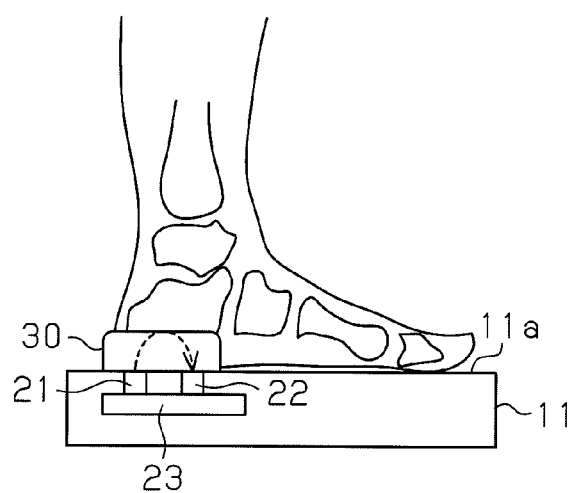

Although not particularly mentioned above, in the preferred embodiment, the bone density meter 20 may include, for example, a light shield that shields out external light to prevent the external light from mixing with the light emitted from the light emission unit 21 and light propagated in the body. For instance, when applying the light shield to the preferred embodiment, as shown in FIGS. 6A and 6B, a U-shaped light shielding wall 30 may be arranged for each of the user's heels at the rear of the footrest 12 to cover the periphery of the heel K. It is preferable that the light shielding wall 30 be a black elastic body formed from urethane or the like. The light shielding wall 30 shields the light required for bone density measurement from light that would act as noise.

For example, the light shielding wall 30 prevents light used for lighting or the like from entering the heel K. This further ensures accurate bone density measurement.

Figure 7:
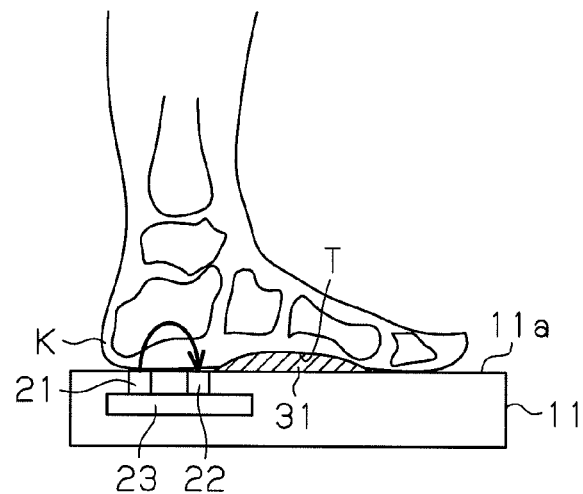
FIG. 7 is a schematic diagram showing a bone density meter in a further example.

Further, referring to FIG. 7, an arched light shield 31 may be formed in conformance with the arch T of a foot on the upper surface 11a of the footrest 12 at a location at which the arch T would be positioned. The light shield 31 would prevent external light used for lighting or the like from entering the heel K through a gap formed by the arch T. This further ensures accurate bone density measurement.

Figure 8A:
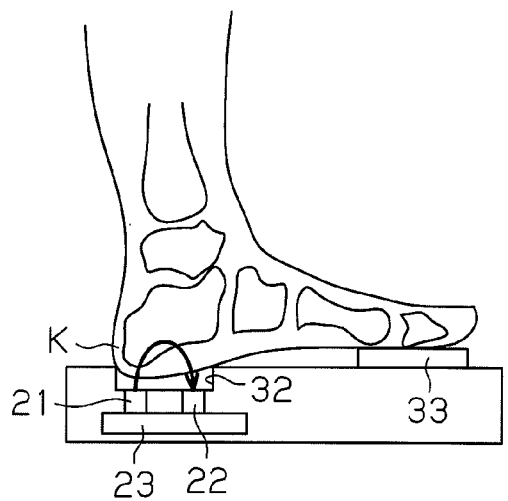
FIGS. 8A and 8B are schematic diagrams showing a bone density meter in a further example.
Figure 8B:
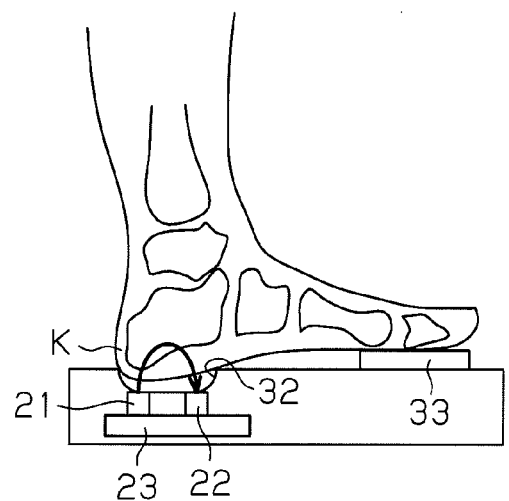

Additionally, for example, as shown in FIG. 8A, the platform 11 may include a recess 32 extending downward from the upper surface 11a to shield the light emission unit 21 and the light reception unit 22 from external light. When a foot is placed in the recess 32, the light emission unit 21 and the light reception unit 22 are protected from external light. This shields the light required for bone density measurement from external light, that is, light that would act as noise. Thus, accurate bone density measurement is further ensured. In this case, the arrangement of a projection 33, which has a predetermined height, near the toes would allow for measurements to be conducted with the heel K in a stable state. Moreover, referring to FIG. 8B, the shape of the recess 32 may be curved in conformance with the heel K so that the heel K can be comfortably fitted to the recess 32.

The light emission unit 21 and the light reception unit 22 may be arranged near the toes to measure the bone density at the toes. In this case, a recess is formed for each toe and shaped in conformance with the toe to measure the bone density of the toe.

Figure 9A:
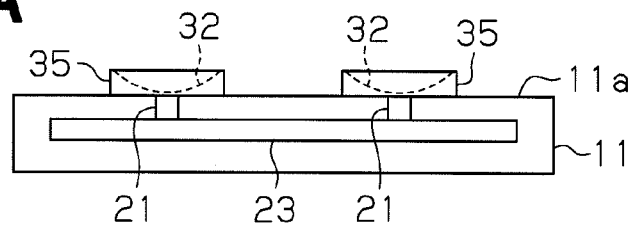
FIGS. 9A and 9B are schematic diagrams showing a bone density meter in a further example.
Figure 9B:
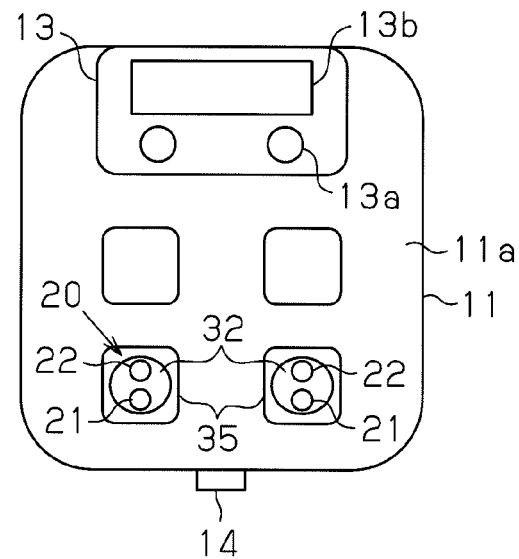

As shown in FIGS. 9A and 9B, a projection 35 may be arranged on the upper surface 11a of the platform 11 for each of the user's heels. The projection 35 may include a recess 32. A structure similar to that of FIGS. 9A and 9B may also be provided for the toes.

Figure 10:
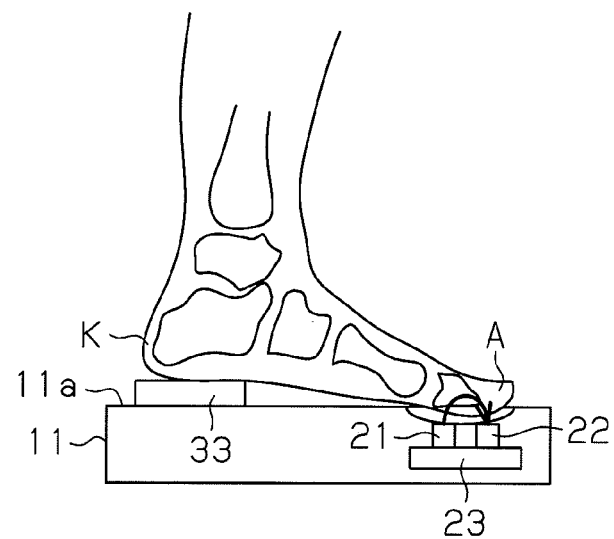
FIG. 10 is a schematic diagram showing a bone density meter in a further example.
Figure 14:
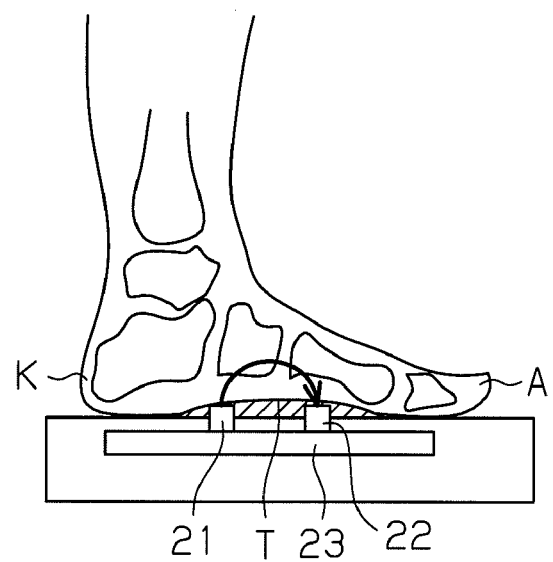
FIG. 14 is a schematic diagram showing a bone density meter in a further example.

In the preferred embodiment, the bone density is measured at the heel, which is a portion where the subcutis is thin. However, the bone density may be measured, for example, at the toes A as shown in FIG. 10 or at the arch T as shown in FIG. 14. Alternatively, the bone density may be measured at the waist bone, shoulder joint, elbow, shin, projected part of wrist, joint of each finger, ankle, or the like.

Figure 11:
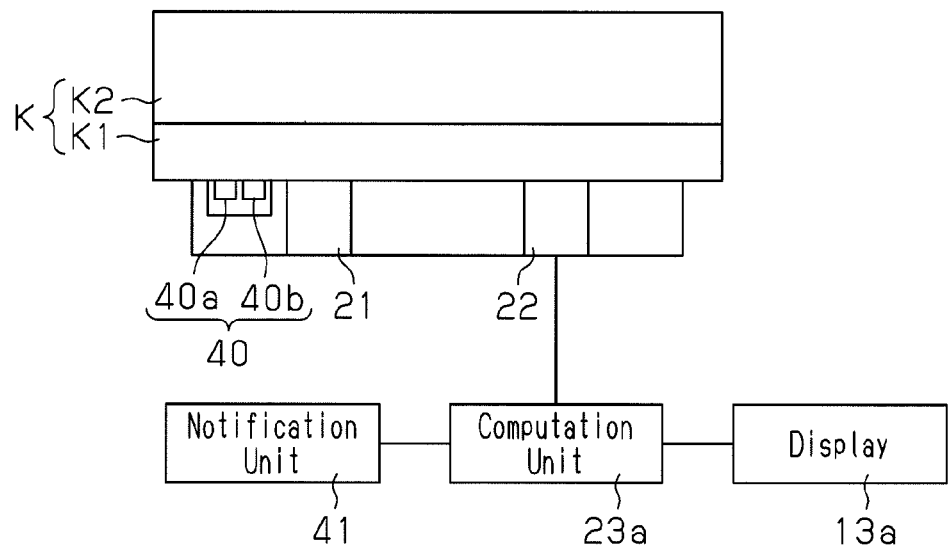
FIG. 11 is a schematic diagram showing a bone density meter in a further example.

Although not particularly mentioned above, in the preferred embodiment, a bone density meter may include, for example, an ultrasonic wave device 40 and a computation unit 23a as shown in FIG. 11. The ultrasonic wave device 40 serves as a measurement unit for measuring the thickness of the subcutis. The computation unit 23a serves as a determination unit for determining whether or not the thickness of the subcutis is 10 mm or less based on the measurement result of the ultrasonic wave device 40. The bone density meter may also include a notification unit 41 which provides notification through audio or a display of whether or not the thickness of the subcutis is suitable for measurement based on the determination result of the computation unit 23a. The ultrasonic wave device 40 includes, for example, a transmitter 40a and a receiver 40b. In this case, for instance, the thickness of the subcutis is measured from the time in which the ultrasonic waves transmitted from the transmitter 40a are reflected by the surface of the heel bone K2 (refer to FIG. 3) and received by the receiver 40b. In this structure, light is emitted from the light emission unit 21 and received by the light reception unit 22, while detecting relatively thin portions of the subcutis at which the thickness is 10 mm or less. This ensures further accurate measurement of the bone density. In addition to using light or ultrasonic waves, the subcutis may be mechanically pinched to measure the thickness of the subcutis. Further, the calculation of the bone density may be started by the computation unit 23a without the issuance of a notification indicating whether or not the thickness of the subcutis is suitable for bone density measurement when it is determined that the thickness of the subcutis is 10 mm or less.

In the preferred embodiment, the light reception unit 22 is formed by a single photodiode but may be formed instead by a plurality of light reception elements (photodiodes). This suppresses deviations in the measurement values of the bone density caused by errors in the light reception amount that may occur in the light reception elements. The light reception element of the light reception unit 22 is not limited to a photodiode and may be a phototransistor. It is only necessary that the light reception element be able to receive the light emitted from the light emission unit 21.

Figure 12:
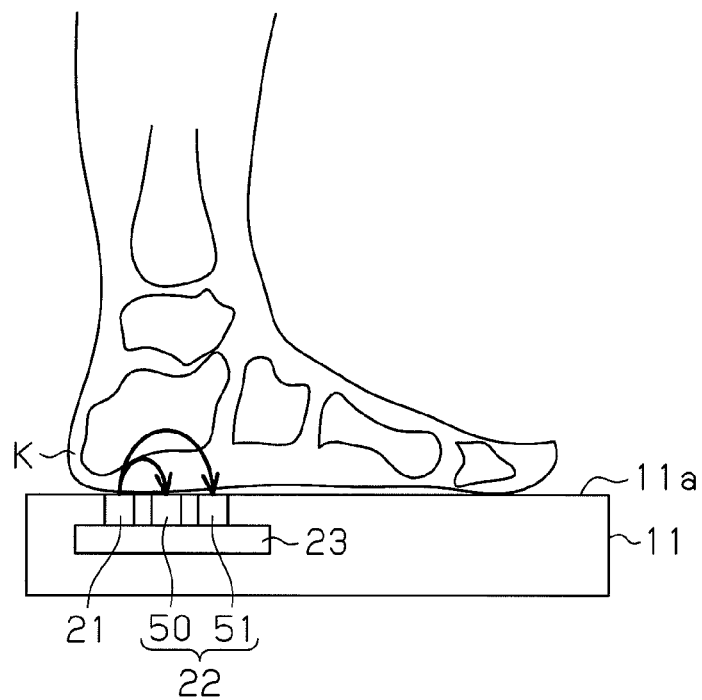
FIG. 12 is a schematic diagram showing a bone density meter in a further example.

Furthermore, as shown in FIG. 12, the light reception unit 22 may include a first light reception element 50 and a second light reception element 51. The first light reception element 50 is located closer to the light emission unit 21 than the second light reception element 51. In this case, the computation unit 23a, which serves as a bone density calculation unit, calculates the bone density from the light amount ratio of the first light reception element 50 and the second light reception element 51. In detail, the light receiving elements 50 and 51 are arranged at positions separated from the light emission unit 21 by different distances to receive light propagated through different light paths in the body. For example, the first light reception element 50, which is located closer to the light emission unit 21, receives light propagated through a shallow portion in the body (mainly, the subcutis). The second light reception element 51, which is located farther from the light emission unit 21, receives light propagated through a deep portion in the body (mainly, the subcutis and bone). The computation unit 23a calculates the bone density from the ratio of the amount of light received by the first light reception element 50 and the amount of light received by the second light reception element 51. This suppresses the influence of the skin color of the body surface or state of the subcutis on the bone density measurement and allows for the bone density to be calculated with further accuracy.

Although not particularly mentioned above, in the preferred embodiment, the computation unit 23a may measure the bone density from the left and right foot soles to calculate the balance of the left and right bone densities. Further, the display 13b may show the bone density balance calculated by the computation unit. The computation unit 23a may also calculate the average value of the bone densities obtained from the left and right foot soles. In this case, the display 13b may show the average value of the bone density calculated from the computation unit 23a.

In the preferred embodiment, the display 13b shows (provides notification of) the bone density measurement result. The bone density measurement result may also be provided with audio output.

Figure 13:
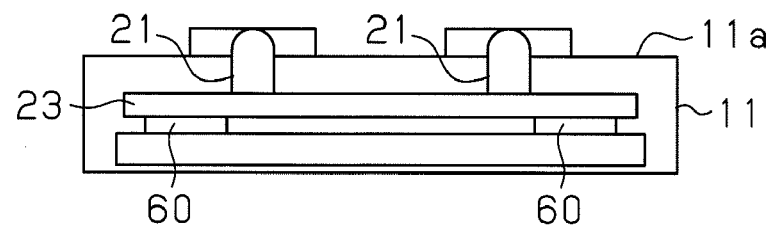
FIG. 13 is a schematic diagram showing a bone density meter in a further example.

Although not particularly mentioned above, in the preferred embodiment, for example, as shown in FIG. 13, a load sensor 60 may be arranged under the microcomputer 23. When the load sensor 60 detects weight that is greater than or equal to a predetermined value, the bone density measurement is started. In this case, the measurement start button 13a may be eliminated from the operation unit 13.

Although not particularly mentioned above, in the preferred embodiment, for example, the microcomputer 23 may include a memory (not shown) storing a database associating bone density with age, height, and weight to calculate and show the user's bone age. Further, an estimated bone density of the entire body may be calculated from the bone density of the sole.

The light emission unit 21 and the light reception unit 22 do not have to be arranged on the platform 11. For example, the light emission unit 21 and the light reception unit 22 may be held on a user's body so as to be in direct contact with the user's body.

The present examples and embodiments are to be considered as illustrative and not restrictive, and the invention is not to be limited to the details given herein, but may be modified within the scope and equivalence of the appended claims.

What is claimed is:

1. A bone density meter for measuring bone density of a user, the bone density meter comprising:
   a light emission unit which emits light toward a surface of the body of the user;
   a light reception unit which receives the light emitted from the light emission unit toward the body surface and propagated through a portion of the body that includes bone; and
   a bone density calculation unit which determines the bone density based on the amount of light received by the light reception unit;
   wherein the light emission unit emits light toward the body surface at a portion having a thin subcutis, and the light reception unit receives the light propagated through the portion of the body that has the thin subcutis,
   the bone density meter further comprising a determination unit which determines whether or not the subcutis at the body surface has a thickness of 10 mm or less,
   wherein when the determination unit determines that the subcutis at the body surface has the thickness of 10 mm or less, the bone density calculation unit determines the bone density based on the amount of light propagated through the subcutis having the thickness of 10 mm or less and received by the light reception unit.

2. The bone density meter according to claim 1, wherein the light emission unit emits light toward a foot sole of a person, which is the body surface.

3. The bone density meter according to claim 1, wherein the light emission unit emits light having a wavelength in the range of 500 nm to 2500 nm.

4. The bone density meter according to claim 1, further comprising:
   a light shield which shields out external light to prevent the external light from mixing with the light emitted from the light emission unit and light propagated in the body.

5. The bone density meter according to claim 1, further comprising:
   a platform on which a person stands with his or her feet, with the platform including an upper surface including a downwardly extending recess;
   wherein the light emission unit and the light reception unit are arranged in the recess and protected from external light.

6. The bone density meter according to claim 1, wherein the light reception unit includes a plurality of light reception elements, and the bone density calculation unit determines the bone density based on the received amount of light received by each of the light reception elements.

7. The bone density meter according to claim 6, wherein:
   the plurality of light receiving elements includes a first light reception element and a second light reception element, in which the first light reception element is located closer to the light emission unit than the second light reception element; and
   the bone density calculation unit determines the bone density from a ratio of the light received by the first light reception element and the light received by the second light reception element.

* * * * *

UNITED STATES PATENT AND TRADEMARK OFFICE
CERTIFICATE OF CORRECTION

PATENT NO. : 8,352,017 B2
APPLICATION NO. : 12/582231
DATED : January 8, 2013
INVENTOR(S) : Kazuhiro Ide Page 1 of 1

It is certified that error appears in the above-identified patent and that said Letters Patent is hereby corrected as shown below:

On the title page, item (73), should read:

-- Assignee: Panasonic Corporation (JP) --

Signed and Sealed this
Third Day of September, 2013

Teresa Stanek Rea
*Acting Director of the United States Patent and Trademark Office*